US008689793B2

United States Patent
Kring (10) Patent No.: US 8,689,793 B2
(45) Date of Patent: Apr. 8, 2014

(54) METHOD AND APPARATUS FOR RESTRAINING A PATIENT'S LEG DURING LEG SURGICAL AND INTERVENTIONAL PROCEDURES

(76) Inventor: Bob Kring, Longwood, FL (US)

(*) Notice: Subject to any disclaimer, the term of this patent is extended or adjusted under 35 U.S.C. 154(b) by 10 days.

(21) Appl. No.: 13/570,624

(22) Filed: Aug. 9, 2012

(65) Prior Publication Data
US 2013/0032156 A1 Feb. 7, 2013

Related U.S. Application Data

(63) Continuation-in-part of application No. 11/566,485, filed on Dec. 4, 2006, now abandoned.

(60) Provisional application No. 60/845,833, filed on Sep. 19, 2006, provisional application No. 60/816,842, filed on Jun. 27, 2006, provisional application No. 60/794,164, filed on Apr. 24, 2006, provisional application No. 60/761,402, filed on Jan. 23, 2006.

(51) Int. Cl.
*A61G 15/00* (2006.01)
*A61F 5/37* (2006.01)
*A47C 20/04* (2006.01)
*A47C 20/02* (2006.01)

(52) U.S. Cl.
USPC ............... 128/845; 128/878; 128/882; 5/650

(58) Field of Classification Search
USPC ............. 128/845, 878, 882; 5/624, 650, 623; 606/203, 202
See application file for complete search history.

(56) References Cited

U.S. PATENT DOCUMENTS

| | | |
|---|---|---|
| 3,027,895 A | 4/1962 | Williams |
| 4,299,213 A | 11/1981 | Violet |
| 4,545,573 A | 10/1985 | Murphy |
| 4,607,885 A | 8/1986 | del Fierro |
| 4,766,892 A | 8/1988 | Kreitman |
| 5,377,510 A | 1/1995 | Smith |
| 7,340,926 B2 | 3/2008 | Kim et al. |
| 2004/0168246 A1 | 9/2004 | Phillips |

*Primary Examiner* — Victoria J Hicks
(74) *Attorney, Agent, or Firm* — Garvey, Smith, Nehrbass & North, L.L.C.; Charles C. Garvey, Jr.; Vanessa M. D'Souza (57) ABSTRACT

An improved method and apparatus for restraining a patient's leg during knee surgery or similar procedure features and improved restraining member that is attachable to an operating room table. The restraining member has a lower concave portion that engages the upper portion and sides of the patient's leg. The restraining member has an upper convex portion that is reinforced with a plurality of ridges. The concave portion can be fitted with an inflatable bladder. The concave portion in other embodiments is fitted with a belt arrangement that enables different degrees of constriction to be imparted to the leg.

8 Claims, 9 Drawing Sheets

METHOD AND APPARATUS FOR RESTRAINING A PATIENT'S LEG DURING LEG SURGICAL AND INTERVENTIONAL PROCEDURES

CROSS-REFERENCE TO RELATED APPLICATIONS

This is a continuation in part of U.S. patent application Ser. No. 11/566,485, filed Dec. 4, 2006, which is a nonprovisional patent application of U.S. Provisional Patent Application Ser. No. 60/845,833, filed Sep. 19, 2006, U.S. Provisional Patent Application Ser. No. 60/816,842, filed Jun. 27, 2006, U.S. Provisional Patent Application Ser. No. 60/794,164, filed Apr. 24, 2006, and U.S. Provisional Patent Application Ser. No. 60/761,402, filed Jan. 23, 2006, each of which are incorporated herein by reference and priority of which is claimed.

Priority of U.S. Provisional Patent Application Ser. No. 60/845,833, filed Sep. 19, 2006, incorporated herein by reference, is hereby claimed.

Priority of U.S. Provisional Patent Application Ser. No. 60/794,164, filed Apr. 24, 2006, incorporated herein by reference, is hereby claimed.

Priority of U.S. Provisional Patent Application Ser. No. 60/816,842, filed Jun. 27, 2006, incorporated herein by reference, is hereby claimed.

Priority of U.S. Provisional Patent Application Ser. No. 60/761,402, filed Jan. 23, 2006, incorporated herein by reference, is hereby claimed.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to devices for holding or securing the leg of a patient during knee arthroscopy surgery and any other medical procedures that require immobilizing of a patient's leg. More particularly, the present invention relates to a leg restraining apparatus that is connectable to an operating room table and that holds the patient's leg above the knee during knee surgery or like medical procedures. Even more particularly, the present invention relates to an improved method and apparatus for restraining the leg of a patient above the knee wherein a specially configured restraining member is equipped in one embodiment with an inflatable bladder that interfaces between the restraining member and the patient's leg and in other embodiments, cradles the leg both above and below and in other embodiments, provides an interlocking ratcheting mechanism that enables a surgeon to selectively tighten the device around the patient's leg.

2. General Background of the Invention

During numerous medical procedures, the leg of a patient must be restrained. For example, a patient's leg must be restrained during knee surgery.

There is a prior U.S. Pat. No. 4,766,892 issued to Gary Krietman that discloses a leg restraint device adapted for orthopedic examinations and operating procedures that provides a firm support for a portion of a patient's limb while the limb or joint is manipulated or stressed. The restraint includes a rigid frame which defines a partially enclosed area within which the patient's limb is inserted. The enclosed area of the frame accommodates a blood pressure type air bag cuff which is secured to the frame by a fastener. Restraintive force is applied to the limb and monitored by pressurizing the air bag to a controlled level. In one embodiment, the partially enclosed area is shaped as an inverted "U" and with the operating table providing the bottom closure. In a further embodiment, the frame includes a horizontal weigh which extends along the operating table and terminates at an upward laterally curved jaw. An adjustable medially curved jaw is positioned along the weigh. After the adjustable jaw has been positioned, the air bag is pressurized to restrain the limb.

The present invention is an improvement of the device shown in the Krietman patent 4,766,892.

BRIEF SUMMARY OF THE INVENTION

The method and apparatus of the present invention incorporates the use of a polycarbonate materials combined with a air bladder to fixate the leg for the purposes of a medical procedure, such as knee arthroscopy and other procedures that include but are not limited to EP studies, vascular intervention via catheters, where the leg is required to remain immobile to facilitate the medical procedure.

The apparatus of the present invention is unique in its concept and structural design, incorporating proprietary structural ridges and support biases, to provide the stiffness and strength characteristics to withstand a minimum of 50 lbs lateral force when flexing valgus and varus angle pressure on the knee joint for arthroscopic knee surgery exposure.

The present invention utilizes an intricate design of Celstran ridges, supports, cross members, and diagonal supports.

The apparatus of the present invention is designed to be both a "disposable leg restraint", and/or a re-useable device in those markets that are not suited for a disposable device. The device weighs between 1 and 1.5 lbs, and is made of about 60% glass polycarbonate material(s).

The present invention is light weight, can be disposable, and negates any cross contamination potential for infection and affords direct access to all points of the knee joint. The apparatus of the present invention provides ease of use and set-up, cost effectiveness by avoiding re-sterilization, cleaning, and administrative costs such as record keeping and liability costs.

The apparatus of the present invention does not act as a tourniquet, and allows for continuation of procedure during long cases requiring release of tourniquet, permits limited blood flow-safety factor. The apparatus of the present invention provides enhanced patient comfort and safety via air bladder that insures equal distribution of stress forces. The apparatus of the present invention can be sterile draped and is readily removable during surgical procedure (w/o breaking sterility) extending operative field.

The apparatus of the present invention can be manufactured as a single molded piece and/or a two section piece incorporating a metal stem (SS/titanium/etc) attached to a polycarbonate arc that supports the air bladder cushion system for immobilizing the leg.

The materials can comprise 60% long strand glass and polycarbonate plastics (e.g. Celstran PA66-GF60-02-BK) and can be produced in a variety of colors (black, natural, yellow, red, blue).

An optional bottom attachment can be used to connect the proximal portion of the arc and the distal end of the arc, in the event that it might be required to provide addition stiffness to the overall brace. The attachment would be passive, merely clipping into place, and supporting additional lateral force, should it be needed.

The present invention incorporates a unique approach to fixating the leg via two methods. In a first method, a base (e.g. Celestran) with interlocking teeth on both sides of the base engage two semi circular pieces that complete the encirclement of the leg, around a circular foam padding (adjusts for size). The operator merely tightens the encircling pieces to the desired tension/fixation position by pressing inward and engaging the next set of teeth on the ends of the two encircling pieces.

The tension of encirclement increases the engagement on the teeth since all the pressure is outward keeping the teeth well engaged into one another. To release, one merely pulls upward on the piece with the handle, and the system of encirclement releases pressure totally, allowing for the removal of the device after the procedure. The attached CAD drawings clearly depict the construction and design of the device, alluding to the unique structural supports required to withstand the lateral pressures of knee surgery requirements.

In a second procedure and embodiment, a base that is somewhat larger and more encompassing than "a" provides a more stabilizing structure to attach a ridged belt that serves to encircle the leg, pass through a geared mechanism that has a locking pin to immobilize the gear and fix the belt at the desired point of tension/fixation.

The tension on the belt is achieved by merely pulling downward/outward on the belt as it passes thru the gear and out of the base housing, and at the desired tension is fixed by engaging the locking pin to the gear. This locks the belt in place, and it can not be released without disengaging the locking pin.

The ridged belt can be padded with a foam pad between the belt and the patients leg. Either of these devices can be manufactured as "disposable" devices, and re-useable devices for those markets that do not lend themselves to disposable products. The foam pads would be a disposable item helping to eliminate the potential for cross contamination and/or infection on both embodiments. These devices can be manufactured as a single base portion with the above described attachments/components, and are unique in design and concept for fixating a leg for the purposes of providing leg stability for medical procedures such as arthroscopic knee surgery and any other medical procedures that require the use of keeping the leg immobile (such as EP studies, vascular catheter intervention-angioplasty and/or stent placement). The first embodiment involves the use of an air bladder and does not totally encircle the leg tension. The second embodiment does in fact encircle the leg and does perform a limited tourniquet effect, while not employing the air bladder. Both embodiments are for practical purposes, aside of design and mechanical function, provide the same features, benefits and advantages. Both can be disposable in nature or re-useable as well. The re-useable model in both embodiments would incorporate a disposable feature. The "air bladder" could be a disposable item. The foam pad would be a disposable item. When designated as a single use device, the entire device would be disposed of after each use.

The present invention includes a limb restraining apparatus for use in combination with a table upon which a patient is resting, comprising: a restraining member removably attached to the table, the restraining member being an integrally molded plastic member having a curved underside concave portion that is positioned to cradle the patient's leg from a position above the patient's leg; the restraining member preventing substantial movement of the patient's limb while allowing movement and manipulation of a distal limb section; a flexible support attached to the concave portion of the restraining member; and the upper surface of the restraining member being a convex surface that is reinforced with a plurality of webs that intersect to form acute angles.

Preferably, flexible support is an inflatable cuff.

Preferably, the present invention further comprises a cradle that removably fits the restraining member, the cradle having an upwardly facing concavity that cradles the patient's leg from below.

Optionally, the restraining member is of a polycarbonate material.

Optionally, the restraining member is of a glass polycarbonate blend.

Optionally, the restraining member is of in excess of 50% long strand glass and polycarbonate plastic material.

Preferably, the cuff includes an inflation stem, the restraining member including an aperture, the stem extending through the aperture to facilitate inflation.

The present invention includes a method of accessing areas of a limb joint for insertion and manipulation of arthroscopic instruments during anthroscopic examination or surgery, the method comprising the steps of: confining a first zone of a limb with a restraining member that has a downwardly facing concavity that covers the top and at least part of the sides of the limb, said restraining member including on the inside an air bag cuff, the first zone being positioned between the patient's body and the joint, said restraining member including on the outside a plurality of structural ridges that form multiple acute angles; immobilizing the air bag cuff; inflating the cuff to a minimum predetermined pressure to restrain the first zone from movement; monitoring and maintaining the inflating pressure while stressing the limb joint, the stressing of the joint being attained by applying forces to a second zone of the limb, the second zone being spaced from the joint in a direction away from the patient's body.

Preferably, the limb is a leg, the joint comprising a knee joint, the first zone comprising a portion of a thigh, the step of immobilizing the air bag cuff comprising immobilizing the cuff adjacent the top and opposite sides of the thigh.

Preferably, the confining step includes positioning the cuff only around the top and sides of the thigh, the underside of the thigh being free of contact with the inflated cuff.

Preferably, the joint is stressed by applying rotational stress to the second zone relative to the first zone.

Preferably, the step of immobilizing the cuff comprises fixing the cuff with respect to a rigid frame, the frame being operatively positioned to overlie the air bag cuff, the fixing step comprising peripherally securing the cuff to the frame, the frame being spaced from the first zone.

The present invention includes a method of restraining a portion of a limb of a patent resting upon a surgical table for orthopedic examination and operating procedures upon a joint of the limb, the method comprising the steps of: providing a restraining member having a rigid support that surrounds the top and sides of the limb to be restrained, said restraining member having an upper convex surface reinforced with a plurality of intersecting ridges and a lower concave surface that engages a patient's leg, and an inflatable cuff on the lower curved surface; registering the restraining member with a first zone of the limb, the first zone being spaced from the joint in a direction towards the patient's torso by adjustably anchoring the rigid support means to the table at a selected position along the length of the table, the support means being out of direct contact with the limb; peripherally confining the first zone of the limb except for an underside portion of the first zone resting upon the surgical table with the inflatable cuff; applying restraintive force to the first zone by inflating the cuff to a pressure while immobilizing portions of the cuff spaced from the first zone of the limb with the rigid support means; monitoring and maintaining the inflated pressure of the cuff for the duration of the operating procedure; and separating portions of the joint to permit the insertion and manipulation of arthroscopic instruments by applying controlled forces to a second zone of the limb, the second zone being spaced from the joint in a direction away from the first zone.

Preferably, the cuff includes an outer periphery, the step of inflating and immobilizing the cuff includes the step of anchoring the cuff to the restraining member.

Preferably, the restraining member includes a plastic frame having a depending leg, the step of anchoring including anchoring the restraining member to the table by inserting the flange into a slot which provided on the table.

The present invention includes a method of stabilizing and rendering immobile the thigh area of a patient for cardiovascular intervention procedures involving the placement of catheters and/or instruments in the patient's cardiovascular system via the femoral arterial vessel, whereby catheter placement and maintenance of position is vital to successful angioplasty intervention and/or placement of arterial stents.

The present invention includes a limb restraining apparatus for use in combination with a table upon which a patient is resting, comprising: a restraining member removably attached to the table, the restraining member being an integrally molded plastic member having a curved underside concave portion that is positioned to cradle the patient's leg from a position above the patient's leg; the restraining member preventing substantial movement of the patient's limb while allowing movement and manipulation of a distal limb section; a flexible belt attached to the restraining member, the belt extending about 360 degrees for encircling and holding a patient's leg; and interlocking portions of the belt enabling the belt to adjust to legs of differing sizes.

Preferably, the belt has multiple sections.

Preferably, the belt has interlocking toothed portions.

Preferably, the belt has a handle at one end portion for enabling tension to be applied to the belt.

Preferably, the belt has belt teeth on a surface of the belt and further comprising a toothed wheel on the restraining member that engages the belt teeth.

Preferably, the toothed wheel can be rotated to tighten or loosen the belt about a patient's leg.

Preferably, the belt has teeth on a belt outer surface, the belt having an inner surface that engages the patient's leg.

Preferably, there is a locking device that locks movement of the belt and wheel in a selected position.

Preferably, the locking device comprises aperatures on the wheel and a locking pin that can interlock with a selected one of the aperatures.

The present invention includes a tourniquet in order to lower the position of the tourniquet from the high thigh to proximal to the knee joint, thus reducing potential tissue and vascular damage caused by the tourniquet on the upper thigh area.

The present invention can be used for procedures including ACL repairs, arthroscopy meniscus repair, and vascular intervention.

The present invention includes a single device with no moving parts and/or attachments. The present invention does not require added bottom support. The present invention can be used on various patients, including small school soccer players, older athletes, adults and elderly (both slim and obese).

In the present invention, a surgeon can use the device for quick case repairs. Using the device of the present invention, a surgeon can perform a surgery in a seated position. The present invention saves time and costs. Patients benefit from the comfort and stability of the present invention. There is less operative time and lower costs associated with use of the present invention. One other advantage is that the apparatus of the present invention standardizes the arthroscopic procedure approach for every patient. The device is easy to set up and avoids MCL tears during surgery that would occur using another apparatus.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein.

DETAILED DESCRIPTION OF THE INVENTION

Figures 8, 9:
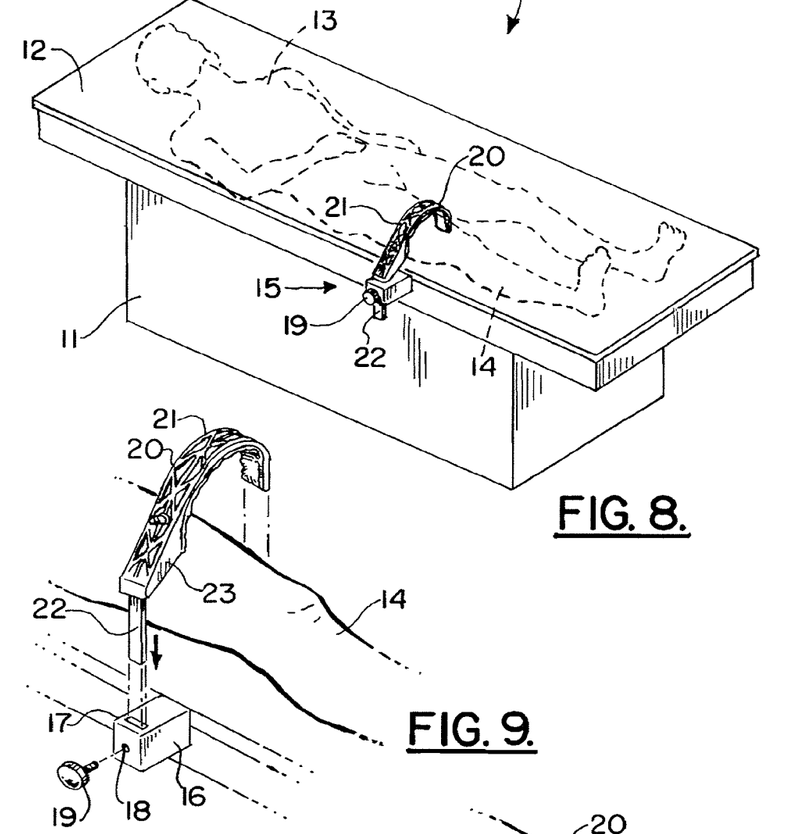
FIG. 8 is a perspective view of the preferred embodiment of the apparatus of the present invention.
FIG. 9 is a fragmentary perspective exploded view of the preferred embodiment of the apparatus of the present invention.
Figure 10:
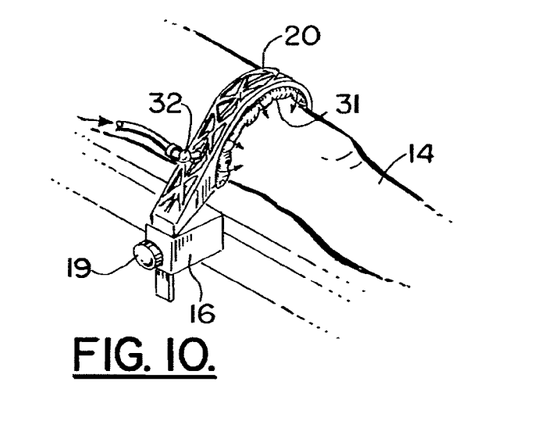
FIG. 10 is a close-up perspective view of the preferred embodiment of the apparatus of the present invention.

FIGS. 1-10 show the preferred embodiment of the apparatus of the present invention designated generally by the numeral 10 in FIG. 8.

Leg restraint apparatus 10 is shown in use in FIG. 8 with a standard operating room table 11 having an upper surface 12 that is receptive of a patient 13. During certain types of orthopedic examination procedures or surgeries, it is necessary to restrain or immobilize a patient's leg 14. A locking mechanism 15 is used in combination with table 11 to hold the leg 14 of a patient 13. The locking mechanism 15 includes a body 16 that is mounted to the table 11. The body 16 provides a vertical slot 17 intersected laterally with an internally threaded opening 18 that is receptive of threaded set screw 19. In this fashion, restraining member 20 or 20A or 20B can be inserted into slot 17 and then clamped and rigidly held to body 16 when set screw 19 is tightened relative to body 16. Operating room tables 11 typically have instrumentation holders for varied apparatus that slide along table rails for positioning, then clamped down in accordance with the patient's height/size.

The restraining member 20, 20A, 20B can include a vertical or mounting flange 22 to which is integrally attached a thickened section 23 and a curved section 21. The restraining member 20, 20A, 20B is of a disposable plastic material, such as of injection molded plastic.

Figure 1:
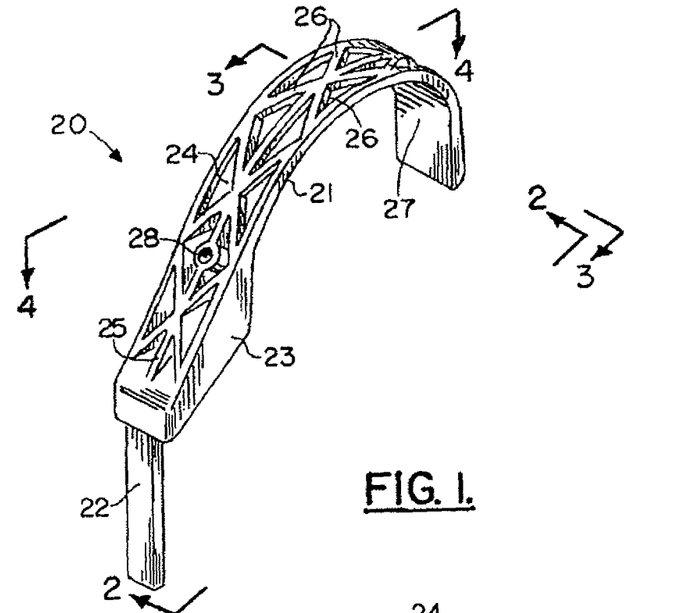
FIG. 1 is a fragmentary perspective view of the preferred embodiment of the apparatus of the present invention.
Figure 2:
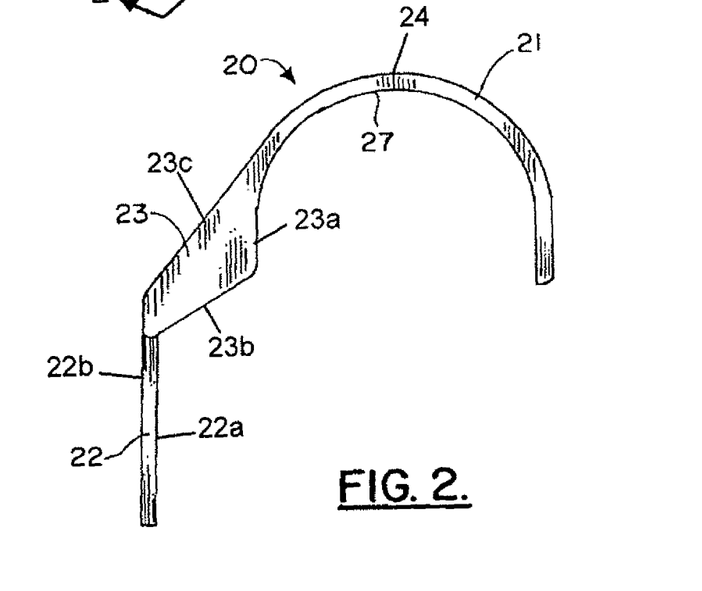
FIG. 2 is a sectional view taken along lines 2-2 of FIG. 1.
Figure 3:
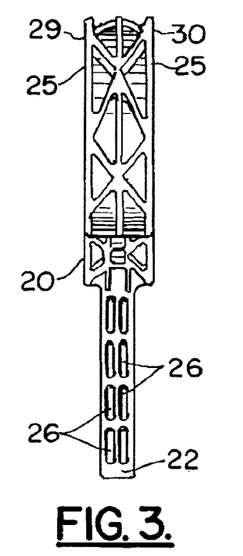
FIG. 3 is a sectional view taken along lines 3-3 of FIG. 1.
Figure 4:
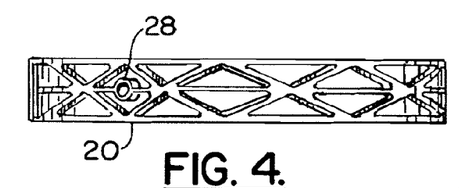
FIG. 4 is a top view taken along lines 4-4 of FIG. 1.
Figure 5:
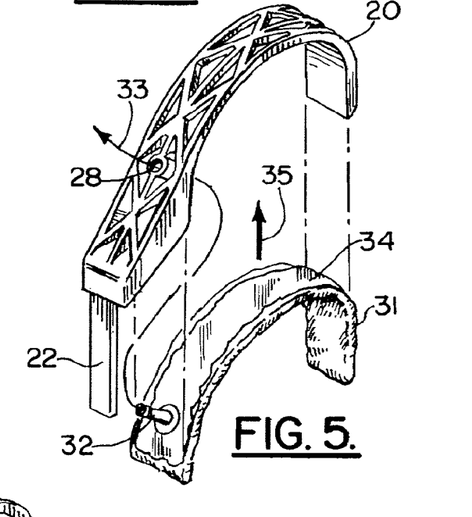
FIG. 5 is a partial perspective view of the preferred embodiment of the apparatus of the present invention.

Curved section 21 provides an upper surface 24 that is reinforced with a plurality of longitudinal webs 25 and a plurality of diagonally positioned webs 26. Lower surface 27 of curved section 21 is preferably smooth, as shown in FIGS. 1 and 2. As seen in FIG. 2, flange 22 has inner surface 22a and outer surface 22b. Thickened section 23 has surfaces 23a, 23b, 23c. Surfaces 22a, 23b form a first obtuse angle. Surfaces 22b, 23c form a second obtuse angle that is larger than the first obtuse angle.

The first obtuse angle created by surfaces 22a and 23b can be preferably 121°-125°, and most preferably 123°. The second obtuse angle created by surfaces 22b and 23c can be preferably 141°-145°, and most preferably 143°. This is preferably the angle range at which the thickened section 23 can be molded and therefore maintain the required rigidity and strength of the brace arc. A different angle could be used based on the different size of the overall arc/brace required, for example, to accommodate smaller or larger leg mass based on the size of a person. Adjusting the angle to a greater or a smaller angle would result in a reduced or increased arc facilitating the overall size of the brace and its use with different leg sizes. This variation of angle ranges would allow for extreme leg sizes and possibly rigidity and strength issues when made with hybrid materials.

The angles as specified herein fit approximately 95% of the population due to the design and use of the air bladder/tourniquet technique. The design is further unique in that this angle arc interface allows for a singular device to address such a large population of patients requiring no further adjustment in order to perform the surgical procedures of meniscectomy and/or ACL repair. Furthermore, it allows for the implementation of a technique that does no require a tourniquet by applying partial restrictive pressure to blood vessels via the air bladder, combined with cold saline, to perform meniscus repairs (the air bladder does not circumvent the patient limb/leg). The aspect that the air bladder does not circumvent the limb is also unique, as other devices with air bladders and/or foam padding circumvent the limb.

Opening 28 extends between the upper surface 24 and lower surface 27. The leg restraining member 20 provides sides 29, 30 that are preferably flat and generally parallel.

In FIGS. 3-10, restraining member 20 is provided with an inflatable bladder 31. The bladder 31 can be supplied with air through a valve 32. As indicated by arrow 33 in FIG. 5, valve 32 can extend through opening 28. Inflatable bladder 31 can be attached to restraining member 20 using adhesive 34 as indicated by arrow 35 in FIG. 5.

Figures 6, 7:
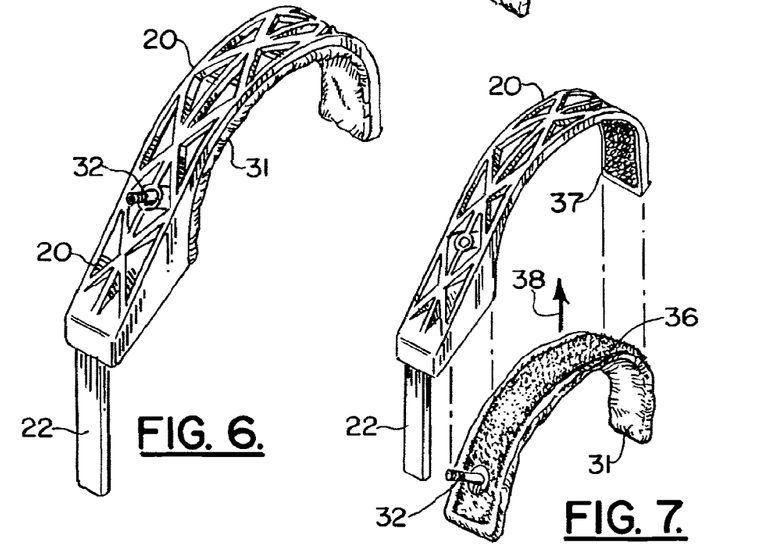
FIG. 6 is a partial perspective view of the preferred embodiment of the apparatus of the present invention.
FIG. 7 is a partial perspective view of the preferred embodiment of the apparatus of the present invention.

Inflatable bladder 31 can be attached to restraining member 20 using a hook and loop or Velcro® type connection, the hook fasteners 36 being attached for example to inflatable bladder 31 while the loop fasteners 37 are provided on the curved surface 27 of restraining member 20. Arrow 38 in FIG. 7 illustrates an attachment of bladder 31 to restraining member 20 using a hook fastener 36 and loop fastener 37 connection.

Figures 11, 12:
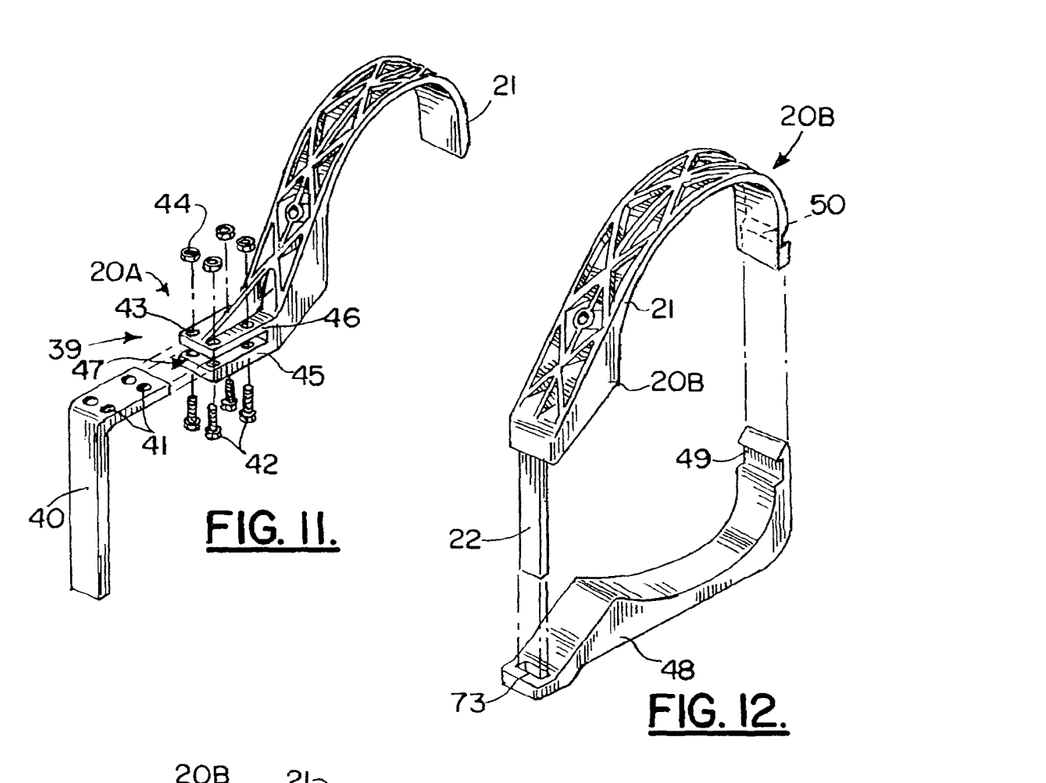
FIG. 11 is a fragmentary perspective view of the preferred embodiment of the apparatus of the present invention illustrating a different construction for the restraining member.
FIG. 12 is a fragmentary perspective view of the preferred embodiment of the apparatus of the present invention illustrating a different construction for the restraining member.
Figure 13:
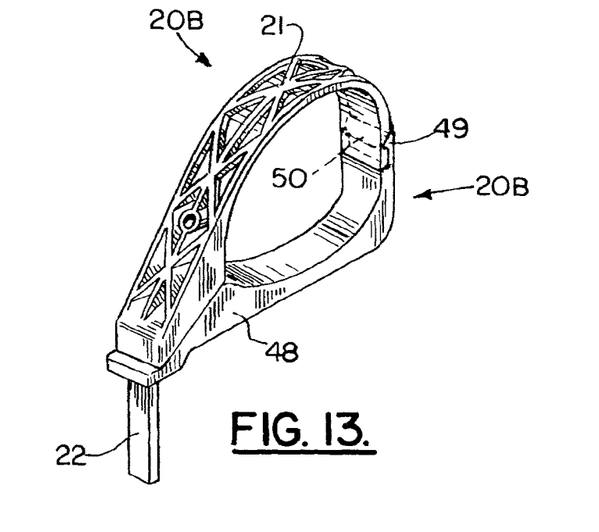
FIG. 13 is a fragmentary perspective view of the preferred embodiment of the apparatus of the present invention illustrating a different construction for the restraining member.

In FIGS. 11-13, other arrangements of a restraining member are shown. In FIG. 11, restraining member 20A provides an ell shaped flanged member 40 that is separate from curved section 21, the parts 21, 40 being joined with a connection 39 that is formed by a plurality of openings 41 in flanged member 40 that align with openings 43 through flanges 45, 46 of curved section 21. The parts 21 and 40 being secured with one or more bolted connections that can include a plurality of bolts 42 and nuts 44 as shown in FIG. 11. Slot 47 provides a space in between the flanges 45, 46 that is receptive of flange member 40.

In FIGS. 12 and 13, the restraining member 20B is first threaded through a leg cradle 48 having a projection 49 that cooperates with and connects to a socket 50 provided on the restraining member 20B. In FIG. 13, the connection has been complete, the vertical flange 22 of restraining member 20B extending through opening 73 of cradle 48 and then being connectable to the body 16 as with the embodiment of FIGS. 1-10.

FIGS. 14-18 show another embodiment of the apparatus of the present invention, designated generally by the numeral 51.

Figure 14:
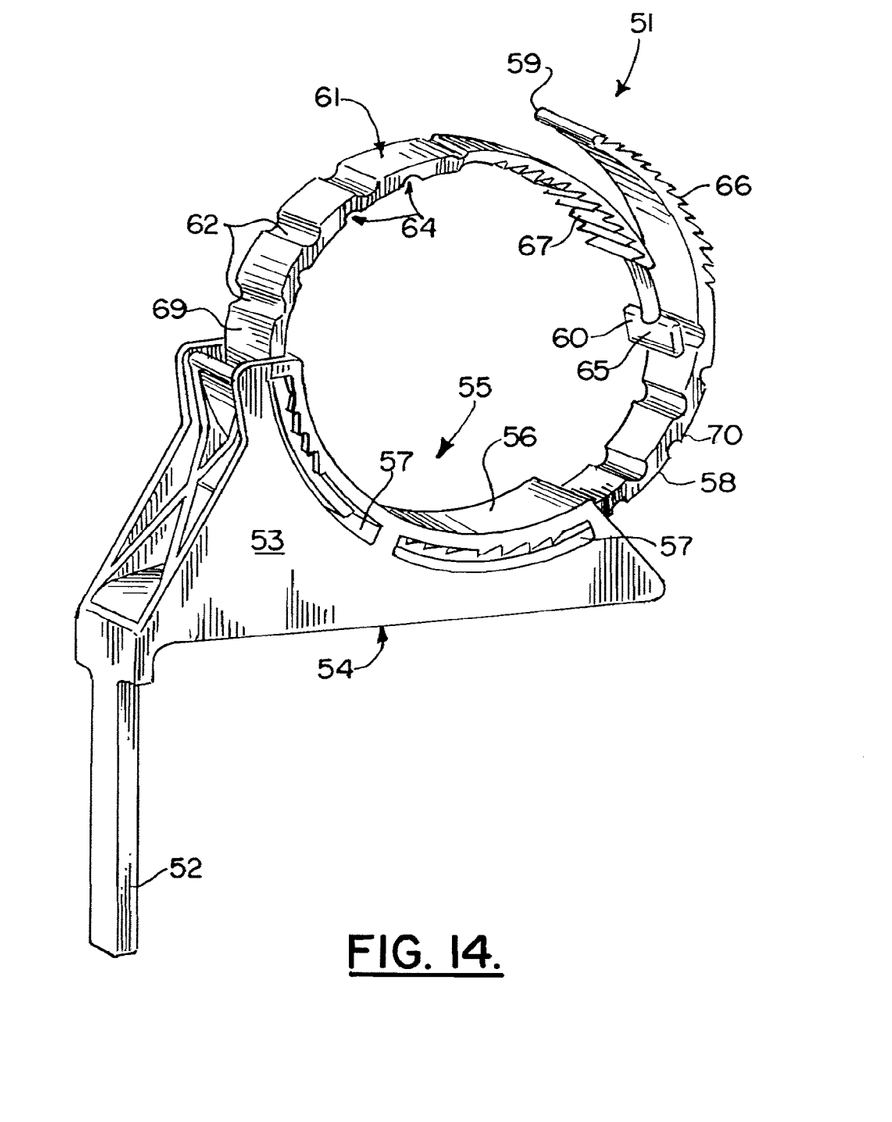
FIG. 14 is a perspective view of an alternate embodiment of the apparatus of the present invention.

Leg restraining apparatus 51 provides a vertical flange 52 that is connectable to the vertical slot 17 of body 16 using threaded set screw 19 and internally threaded opening 18 as with the embodiment of FIGS. 1-13. In FIG. 14, a cradle 53 has a flat underside that can be rested upon upper surface 12 of operating room table 11. Cradle 53 provides a concavity 55 defined by curved surface 56 of cradle 53. Cradle 53 provides a curved slot 57 that is receptive of belt 58. The belt 58 can include multiple belt sections 69, 70.

A belt free end portion 59 forms a connection with another belt free end portion 60. Outer surface 61 of each belt section 69, 70 can be provided with transverse grooves 62 for increasing belt 58 flexibility. Each belt section 69, 70 has an inner surface 63 that is generally smooth and curved as shown. However, the inner surface 63 of each belt 58 or belt section 69, 70 can also be provided with transverse grooves 64 as shown.

The belt free end portion 60 provides a handle 65 that enables a user to tighten the free end portion 60 relative to the free end portion 59. In that regard, the free end portion 59 provides upwardly facing teeth 66, while the free end portion 60 provides downwardly facing teeth 67 as shown in FIGS. 14-18. If the belt 58 is formed of multiple belt sections 69, 70, the curved slot 57 can provide teeth at 74 that form a connection with the teeth 71, 72 of the belt sections 69, 70.

Figure 15:
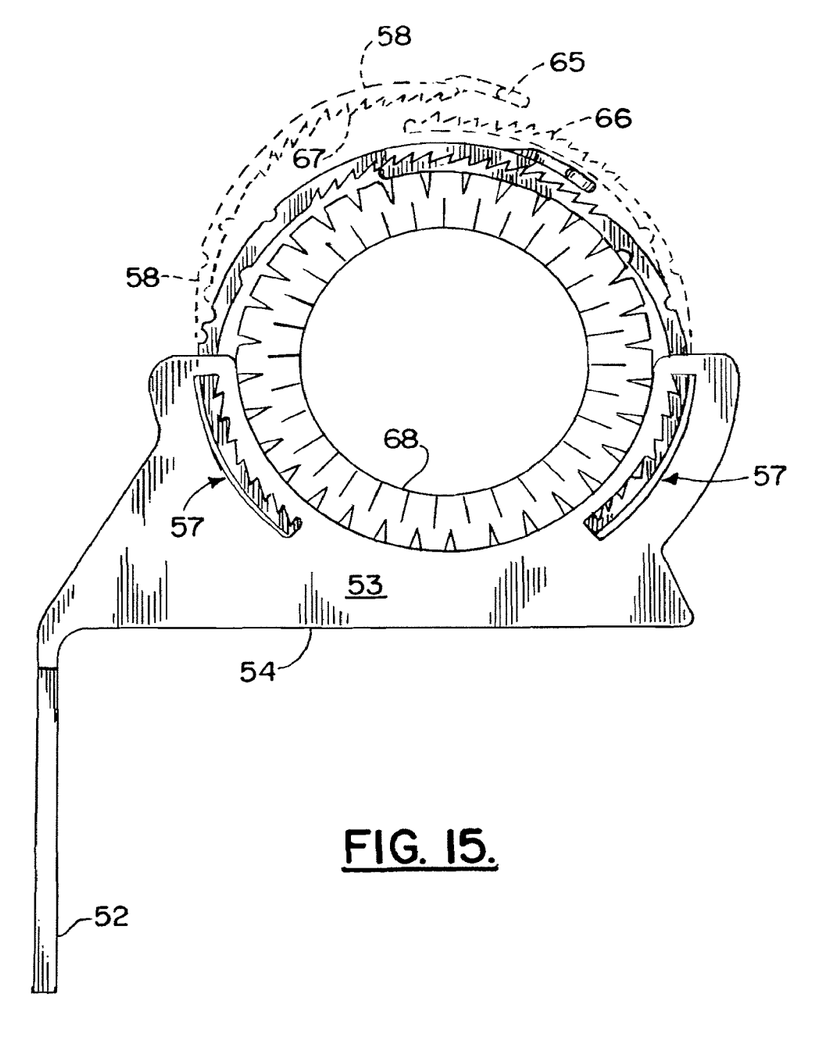
FIG. 15 is a perspective view of an alternate embodiment of the apparatus of the present invention.
Figure 16:
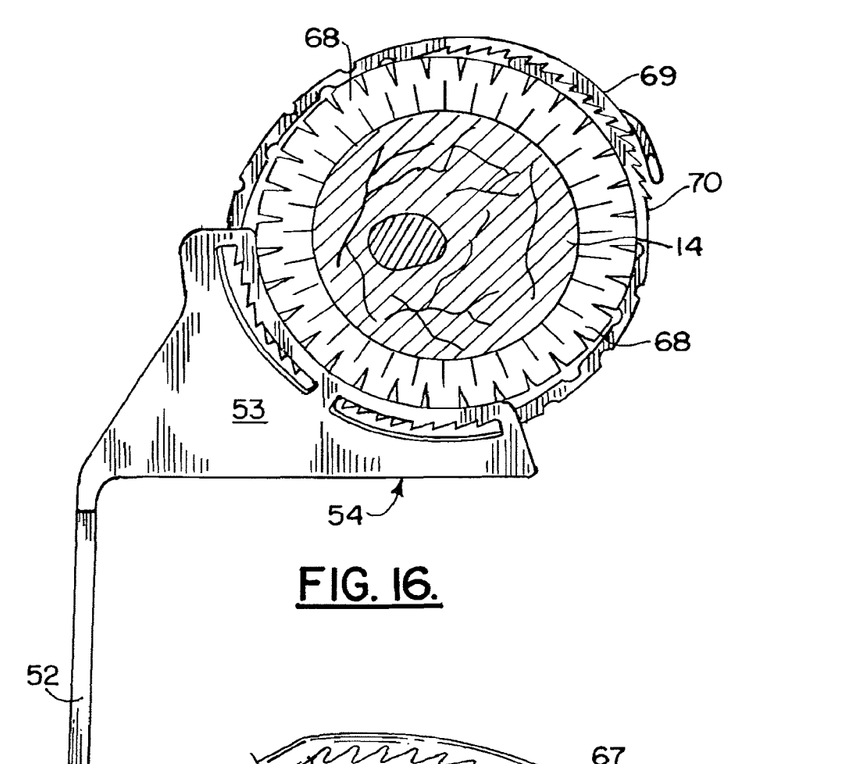
FIG. 16 is a sectional elevation view of the second embodiment of the apparatus of the present invention.
Figure 17:
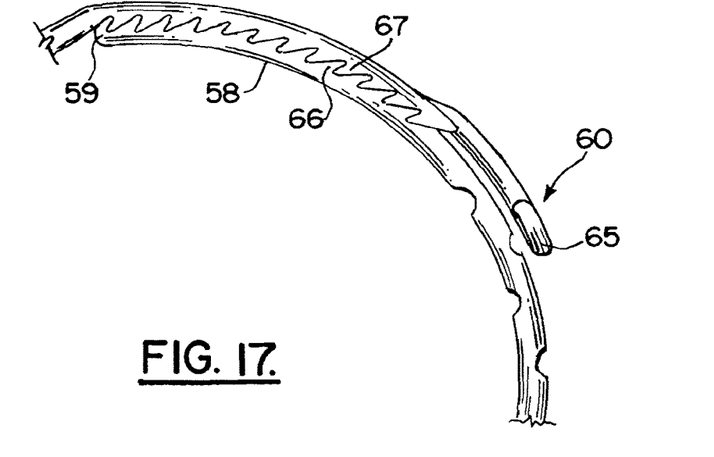
FIG. 17 is a fragmentary sectional view of the second embodiment of the apparatus of the present invention.
Figure 18:
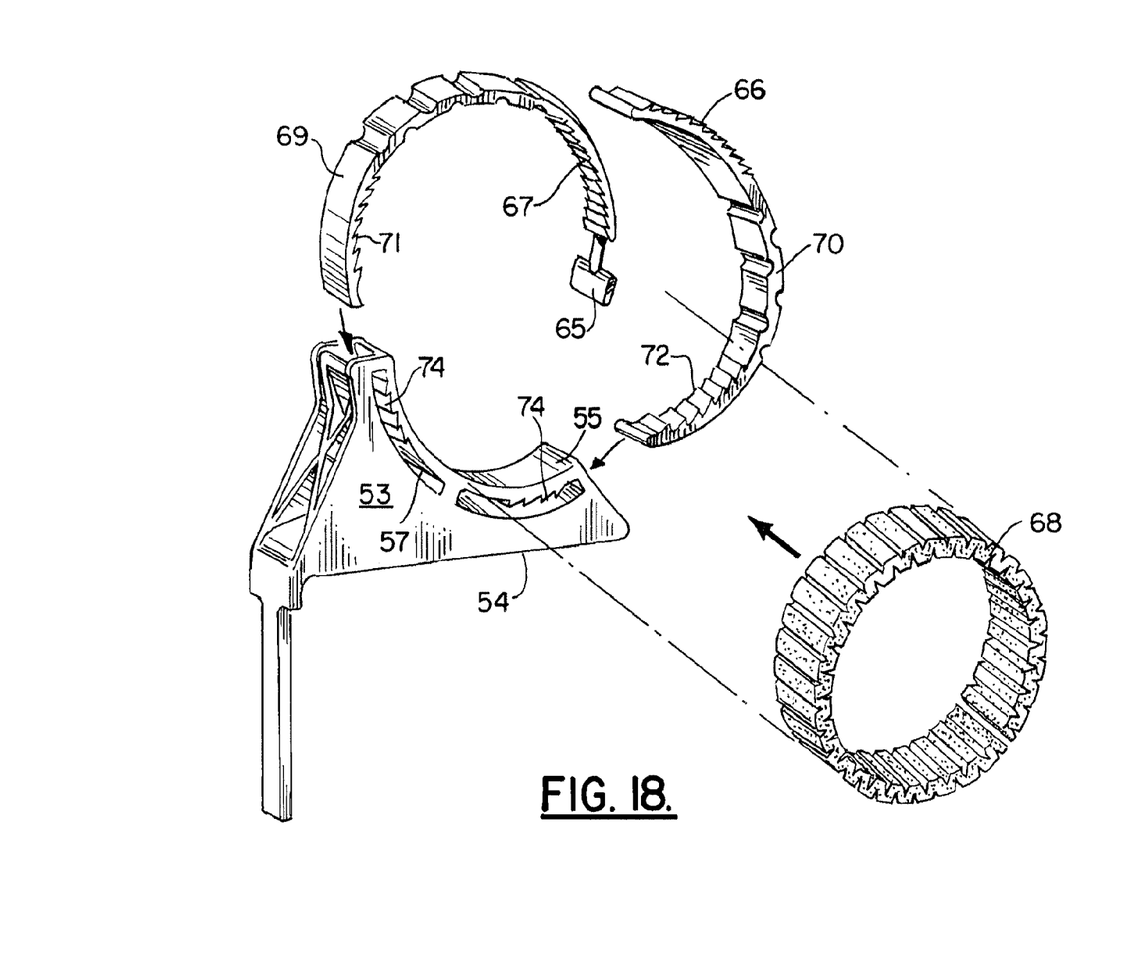
FIG. 18 is an exploded perspective view of the second embodiment of the apparatus of the present invention.

In FIGS. 15-16, the patient's leg 14 is shown secured within the belt sections 69, 70. A donut shaped pad 68 can be placed as an interface between the belt sections 69, 70 and cradle 53 and the patient's leg 14.

Figure 19:
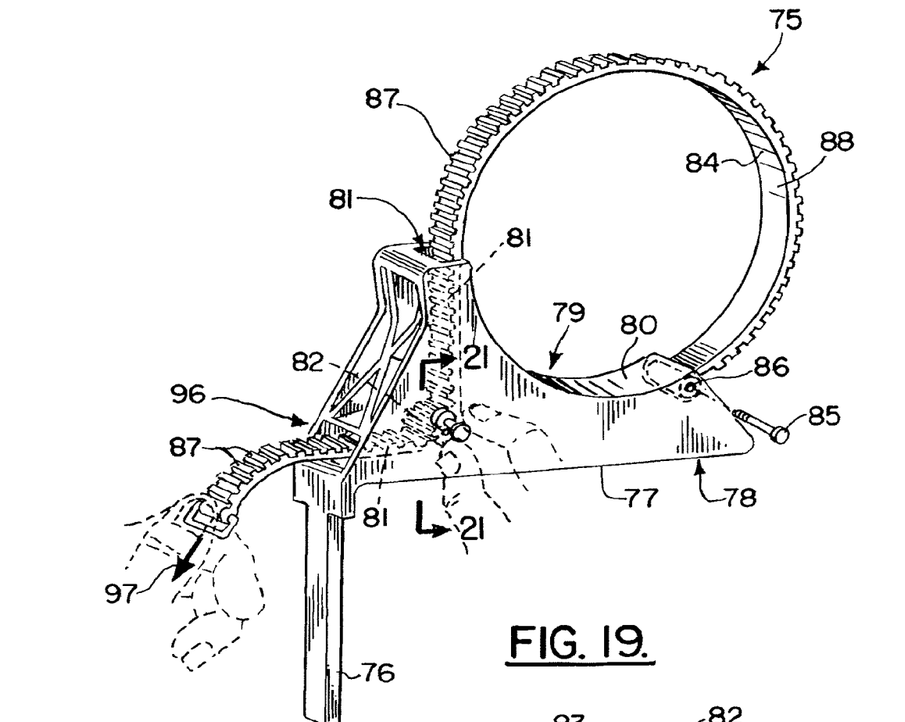
FIG. 19 is a perspective view of a third embodiment of the apparatus of the present invention.
Figure 20:
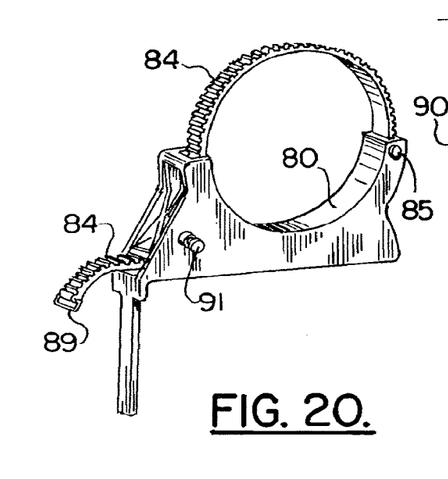
FIG. 20 is a perspective view of a third embodiment of the apparatus of the present invention.
Figure 21:
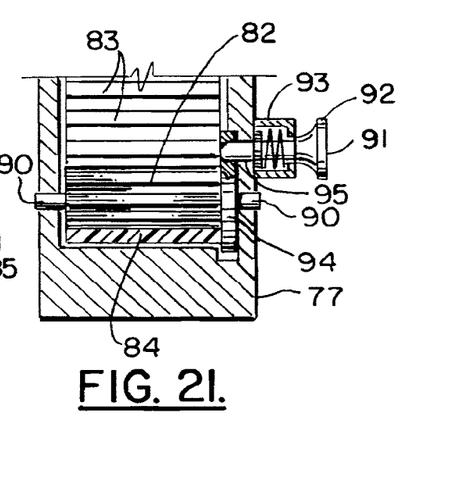
FIG. 21 is a sectional view taken along lines 21-21 of FIG. 19.

FIGS. 19-21 show another embodiment of the apparatus of the present invention. In FIGS. 19-20, leg restraining apparatus 75 provides a vertical flange 76 that is integrally attached to cradle 77. Cradle 77 provides a flat surface or underside 78 that can rest upon the operating room table 11 upper surface 12. Cradle 77 provides a concavity 79 defined by curved surface 80. The curved surface 80 can extend a full 180 degrees as shown in FIG. 20 or can be less than 180 degrees as shown in FIG. 19. An ell shaped channel 81 extends through cradle 77 as shown in FIG. 19. Channel 81 extends to pinion gear 82 and then exits via outlet 96. The free end portion of belt 84 can be gripped at d-ring 89 by a user as shown in FIG. 19, illustrated schematically by the arrow 97. Belt 84 is a toothed belt, having a toothed surface 87 that engages teeth 83 of pinion gear 82. Belt anchor pin 85 anchors belt 84 to cradle 77 as shown in FIGS. 19 and 20. Belt anchor pin 85 is secured to pin opening 86, also extending through an opening at an end portion of the belt 84.

Pinion gear 82 has a gear shaft 90 that is mounted to opposing sides of cradle 77 as shown in FIG. 21. Locking pin 91 can be used to form an interlocking connection with an opening 95 in gear plate 94 that is attached to and rotates with pinion gear 82. Locking pin 91 can provide a knob 92 and spring 93. The spring 93 normally holds the locking pin 91 in a locking position as is shown in FIG. 21. Knob 92 enables a user to pull the pin away from pinion gear 82 for unlocking the pinion gear and enabling a user to tighten the belt 84. When a user releases the knob 92, spring action provided by spring 93 thrusts the locking pin 91 back into engagement with one of the openings 95 in plate 94 of gear 82.

The embodiment of FIGS. 19-21 can also be used with a donut shaped pad 68, as is shown in FIGS. 15-16.

The following is a list of parts and materials suitable for use in the present invention.

PARTS LIST

| Part Number | Description |
| --- | --- |
| 10 | leg restraint apparatus |
| 11 | operating room table |
| 12 | upper surface |
| 13 | patient |
| 14 | leg |
| 15 | locking mechanism |
| 16 | body |
| 17 | vertical slot |
| 18 | internally threaded opening |
| 19 | threaded set screw |
| 20 | restraining member |
| 20A | restraining member |
| 20B | restraining member |
| 21 | curved section |
| 22 | vertical flange/mounting flange |
| 22a | inner surface |
| 22b | outer surface |
| 23 | thickened section |
| 23a | surface |
| 23b | surface |
| 23c | surface |
| 24 | upper surface |
| 25 | longitudinal web |
| 26 | diagonal web |
| 27 | lower surface |
| 28 | opening |
| 29 | side |
| 30 | side |
| 31 | inflatable bladder |
| 32 | valve |
| 33 | arrow |
| 34 | adhesive |
| 35 | arrow |
| 36 | hook fastener |
| 37 | loop fastener |
| 38 | arrow |
| 39 | connection |
| 40 | flanged member |
| 41 | opening |
| 42 | bolt |

-continued

PARTS LIST

| Part Number | Description |
| --- | --- |
| 43 | opening |
| 44 | nut |
| 45 | flange |
| 46 | flange |
| 47 | slot |
| 48 | leg cradle |
| 49 | projection |
| 50 | socket |
| 51 | leg restraining apparatus |
| 52 | vertical flange |
| 53 | cradle |
| 54 | flat underside |
| 55 | concavity |
| 56 | curved surface |
| 57 | curved slot |
| 58 | belt |
| 59 | free end portion |
| 60 | free end portion |
| 61 | outer surface |
| 62 | transverse groove |
| 63 | inner surface |
| 64 | transverse groove |
| 65 | handle |
| 66 | teeth |
| 67 | teeth |
| 68 | pad |
| 69 | belt section |
| 70 | belt section |
| 71 | teeth |
| 72 | teeth |
| 73 | opening |
| 74 | teeth |
| 75 | leg restraining apparatus |
| 76 | vertical flange |
| 77 | cradle |
| 78 | flat underside |
| 79 | concavity |
| 80 | curved surface |
| 81 | ell shaped channel |
| 82 | pinion gear |
| 83 | tooth |
| 84 | belt |
| 85 | belt anchor pin |
| 86 | pin opening |
| 87 | toothed surface |
| 88 | smooth surface |
| 89 | d-ring |
| 90 | gear shaft |
| 91 | locking pin |
| 92 | knob |
| 93 | spring |
| 94 | gear plate |
| 95 | opening |
| 96 | outlet |
| 97 | arrow |

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

The invention claimed is:

1. A limb restraining apparatus for use during knee surgery on a leg of a patient, the leg having an upper portion and an underside and a knee, and in combination with a surgical table upon which the patient is resting, comprising:

a) a restraining member that includes a vertical flange that enables removable attachment to the surgical table, the restraining member being an integrally molded plastic section having a curved member having an upper convex surface and an underside curved concave surface that is positioned to cradle the upper portion of the leg of the patient but not the underside of the leg of the patient said curved member having first and second end portions and attached at said first end portion to an upper portion of said vertical flange, the second end portion of said curved member being a free end portion;

b) the restraining member adapted to prevent substantial movement of the leg of the patient above the knee while allowing movement and manipulation of a distal leg portion of the patient, below the knee;

c) a flexible support attached to the underside curved concave surface of the restraining member, said flexible support extending along the curved member in between said curved member first and second end portions;

d) the restraining member including a thickened portion that forms an interface between the curved member and the vertical flange, the thickened portion including a plurality of surfaces including a first surface that is in communication with the said underside curved concave surface, a second surface that is in communication with the said upper convex surface below said first end portion and a third surface that extends between said vertical flange and said first surface, forming a first obtuse angle with said vertical flange;

e) wherein the thickened portion has an upper tapered portion and a lowered tapered portion and a central portion of maximum thickness;

f) wherein said vertical flange and said second surface define a second obtuse angle that is greater than the first obtuse angle; and g) wherein the restraining member is of a polycarbonate material.

2. A limb restraining apparatus constructed in accordance with claim 1 wherein said flexible support is an inflatable cuff.

3. A limb restraining apparatus constructed in accordance with claim 2 wherein the inflatable cuff includes an inflation stem, the restraining member including an aperture, the inflation stem extending through the aperture to facilitate inflation.

4. A limb restraining apparatus constructed in accordance with claim 1 wherein the restraining member is of a reinforced polycarbonate material.

5. A limb restraining apparatus constructed in accordance with claim 1 wherein the restraining member is of a glass polycarbonate blend.

6. A limb restraining apparatus constructed in accordance with claim 1 wherein the restraining member is of in excess of 50% long strand glass and polycarbonate plastic material.

7. A limb restraining apparatus constructed in accordance with claim 1 wherein the vertical flange has a transverse cross section, and wherein the thickened portion has a transverse cross section that is greater than the transverse cross section of the vertical flange.

8. A limb restraining apparatus constructed in accordance with claim 1 wherein the curved member has a transverse cross section and the thickened portion has a transverse cross section that is greater than the transverse cross section of the curved member.

* * * * *